United States Patent [19]
Harada

[11] Patent Number: 5,042,946
[45] Date of Patent: Aug. 27, 1991

[54] ATOMIC ABSORPTION SPECTROPHOTOMETRIC METHOD AND APPARATUS

[75] Inventor: Katsuhito Harada, Katsuta, Japan

[73] Assignee: Hitachi, Ltd., Tokyo, Japan

[21] Appl. No.: 518,422

[22] Filed: May 2, 1990

[51] Int. Cl.$^5$ ............................ G01J 3/10; G01J 3/42; G01N 21/72

[52] U.S. Cl. .................... 356/307; 356/312; 356/315

[58] Field of Search ............. 356/307, 312, 315, 316

[56] References Cited

U.S. PATENT DOCUMENTS

| | | | |
|---|---|---|---|
| 3,825,344 | 7/1974 | Bonne | 356/307 |
| 4,341,470 | 7/1982 | Parker et al. | 356/307 |
| 4,462,685 | 7/1984 | Smith, Jr. et al. | 356/307 |

FOREIGN PATENT DOCUMENTS 1453189  1/1989  U.S.S.R. ............... 356/307

OTHER PUBLICATIONS

Japanese publication, "Bunkoh Kenkyu" (vol. 35, No. 1, edited by Hidehiro Daidohji, 1986, pp. 42–49).

Primary Examiner—F. L. Evans
Attorney, Agent, or Firm—Antonelli, Terry, Stout & Kraus

[57] ABSTRACT

An atomic absorption spectrophotometric apparatus, which includes a first light source emitting plural specific spectra by changing the current of the first light source into relatively small and large currents, a second light source emitting a continuous spectrum, an atomizer for atomizing a sample, a beam combiner for directing the spectrum emitted from the first light source and the second light source to the atomized sample, a detector for detecting the plural specific spectra and the continuous spectrum which passes through the atomized sample, and a computer for obtaining spectrum absorbances of the plural specific spectra and the continuous spectrum from the outputs of the detector and obtaining a concentration of a specific element on the basis of a combination of the spectrum absorbances. As the sample concentration is calculated from the two spectrums and the continuous spectrum, the background is corrected and at the same time the measuring range of the concentration is expanded so as to obtain the concentration with high accuracy.

10 Claims, 3 Drawing Sheets

ATOMIC ABSORPTION SPECTROPHOTOMETRIC METHOD AND APPARATUS

BACKGROUND OF THE INVENTION

The present invention relates to an atomic absorption spectrophotometric method and apparatus for executing analytical measurement of various substance elements in a sample by adopting an atomic absorption of a light having a specific wavelength and more particularly to the atomic absorption spectrophotometer measuring an absorption spectra of the sample with high accuracy, by measuring plural specific absorption spectra which are generated by changing current of light source and a continuous absorption spectrum.

In a conventional atomic absorption spectrophotometer, the sample is vaporized by a burner or a furnace shaped like a tube, and the vaporized sample is passed through the light from the light source having a specific spectrum and a concentration thereof is detected by measuring the atomic absorption of the light. Such an atomic absorption spectrophotometer is suitable for measuring the concentration of traces of a metallic elements, especially heavy metallic elements.

As there are many other substances with target chemical elements in a frequency area of measuring spectra, the light absorption of the many substances caused by light scattering or molecular absorption etc., occurs so as to result in a measuring error. In order to attain correction of such error, in what is called background correction, absorption spectroscopy using a continuous spectrum, Zeeman atomic absorption spectroscopy and a background correction method using self-reversal of a spectrum line are generally employed.

U.S. Pat. No(s). 5,562,685 and 5,341,470 and Japanese publication "Bunkou Kenkyuu" (Vol. 35, No. 1, edited by Hidehiro Daidohji, 1986, pages 42 to 49) are cited as examples of such a method.

But the conventional technique has the following drawbacks. In the conventional method, a linear area of the detected absorbance of the spectrum is very short so as to narrow a measuring dynamic range of atomic absorption spectroscopy.

SUMMARY OF THE INVENTION

The present invention has been accomplished to overcome the above mentioned problem of the conventional technique.

An object of present invention is in providing an atomic absorption spectrophotometric method and apparatus having a first light source emitting plural specific spectra and a second light source emitting a continuous spectrum, wherein said first light source emits plural specific absorption spectra by changing the current of the first light source by a small current and a large current and measuring the specific absorption spectrum $A_1$ in the small current and the specific absorption spectrum $A_2$ in the large current, and further the continuous spectrum $A_D$ so as to obtain a concentration of the target chemical element from the spectra $A_1$, $A_2$ and $A_D$.

DETAILED DESCRIPTION OF THE PREFERRED EMBODIMENTS

At first in the present invention, a spectrum absorbance is measured by using an atomic absorption analyzing method as in the conventional method when a small current flows in a light source such as a hollow cathode lamp so as to emit a spectrum corresponding to a specific element and the spectrum from the light source passes through an atomized specimen. Here, $A_1$ denotes the absorbance measured in the time when the small current mentioned as above is flown.

Then, the light absorbance is measured when a relatively larger current than the small current flows in the light source and the spectrum from the light source passes through the atomized specimen. Here, $A_2$ denotes the absorbance measured in the time when the larger current mentioned is flown and the absorbance $A_2$ is 10 to 30% of $A_1$.

Figure 3:
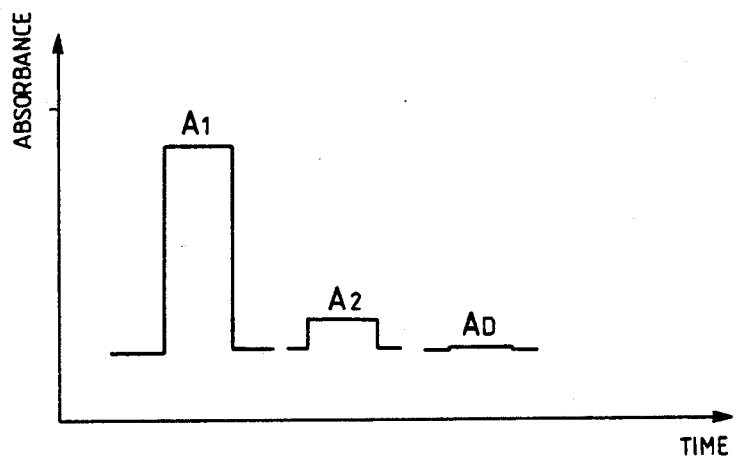
FIG. 3 is a waveform showing absorbance of the spectra which pass through an area of the vaporized sample.

And further, the spectrum absorbance is measured a current flows in when a light source such as a deuterium lamp which emits a continuous spectrum and the continuous spectrum passes through the atomized specimen. Here, $A_D$ denotes the spectrum absorbance in the time when the continuous spectrum is absorbed and the spectrum absorbance $A_D$ becomes less than 0.1% of $A_1$. Such absorbances $A_1$, $A_2$ and $A_D$ are shown in FIG. 3.

In the present invention, a calculation of combinations of the spectrum absorbances $A_1$, $A_2$ and $A_D$ is executed so as to measure a concentration of the element in the sample. The calculation of the combinations is, for example, a subtraction between the spectrum absorbances as follows:

$A_1 - A_2$: 70 to 90% of the spectrum absorbance in the usual atomic absorption analyzing method.

$A_1 - A_D$: almost the same spectrum absorbance as that in the usual atomic absorption analyzing method.

$A_2 - A_D$: 10 to 30% of the spectrum absorbance in the usual atomic absorption analyzing method.

Figure 4:
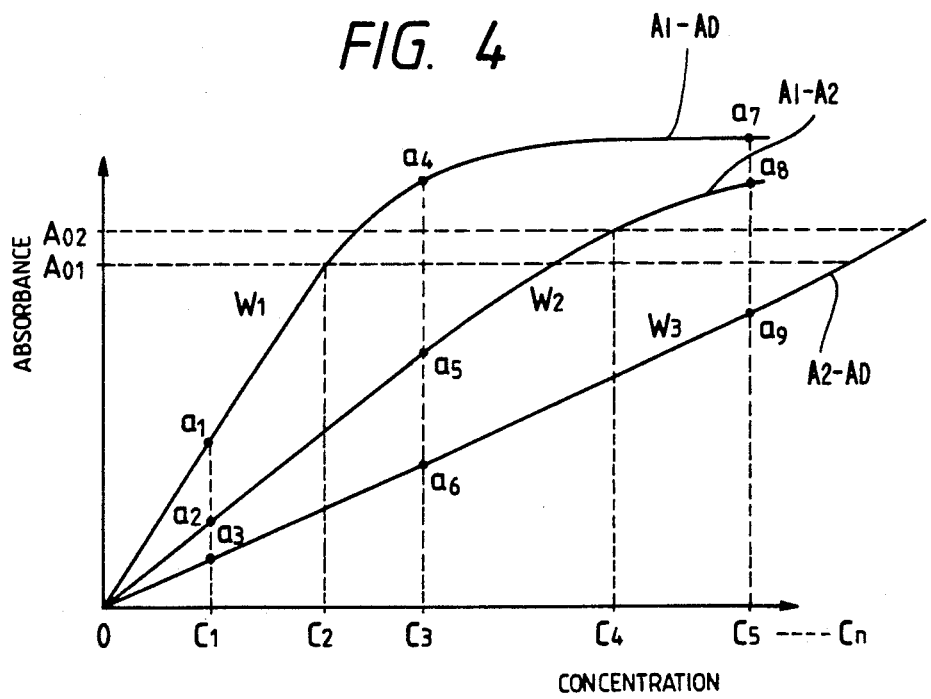
FIG. 4 is a graphical representation of working curves which show the absorbances of the spectra corresponding to concentration of the sample.

FIG. 4 are working curves which shows a spectrum absorbance relation according to a concentration of the atomized sample through which the spectrum passes and $W_1$ denotes a working curve corresponding to the absorbance $A_1 - A_D$, $W_2$ denotes a working curve corresponding to the absorbance $A_1 - A_2$ and $W_3$ denotes a working curve corresponding to the absorbance $A_2 - A_D$. Using the working curves $W_1$, $W_2$ and $W_3$, the concentration of the specimen corresponding to the absorbances can be obtained from the absorbances corrected for the background absorbances. That is to say, in the case of using the working curves $W_1$, $W_3$, $A_D$ is a background correction value and in the case of using the working curve $W_2$, $A_2$ is a background correction value.

As apparent from the working curves $W_1$, $W_2$ and $W_3$ shown in FIG. 4, the working curve $W_1$ which means a subtraction relation $(A_1-A_D)$ has a straight line portion, then the working curve $W_2$ which means a subtraction relation $(A_1-A_2)$ has a longer straight line portion and the working curve $W_3$ which means a subtraction relation $(A_2-A_D)$ has the longest straight line portion. For example, the straight line portion of the working curve $W_3$ is very long in comparison with that of the working curve $W_1$ and makes it possible to measure the concentration of the specimen which is about 10 times higher than that in the case of using the working curve $W_1$. Concerning inclination of the working curves, $W_2$ is more inclined than $W_3$ and $W_1$ is inclined the most of $W_1$, $W_2$ and $W_3$.

In the present invention, measurement of the concentration of the specimen is carried out by selecting the working curve and the selection of the working curve is performed depending on the length of the straight line portion and the inclination of the working curves.

In the specific example shown in FIG. 4, each of the working curves $W_1$, $W_2$ and $W_3$ has the straight line portion in the range of the concentration from 0 to $C_2$, and the measured spectrum absorbance corresponding to the concentration becomes larger in proportion to the inclination of the working curve so that the measuring accuracy of the light absorbance becomes higher and it is preferable to select the working curve $W_1$.

For example, in the case that the spectrum absorbance is at a point $a_1$ of the working curve $W_1$, a point $a_2$ of the working curve $W_2$ or a point $a_3$ of the working curve $W_3$ concerning the same sample concentration $C_1$, the point $a_1$ is selected as the spectrum absorbance. But when the spectrum absorbance $A_D$ of the continuous spectrum is used as the background correction value as in the working curve $W_1$ which means a subtraction relation $(A_1-A_D)$, the background correction is sometimes excessive because of a lot of other elements in the sample, for example, as in the case of analyzing a very small amount of a certain metal mixed with steel or antimony mixed with lead, and in this case the working curve $W_2$ is selected because it is based on an atomic absorption method which corrects the background by a self-reversal method.

In the range of the sample concentration from $C_2$ to $C_4$, the working curve $W_1$ is not straight and the working curve $W_2$ or $W_3$ is selected. In this case, as the working curve $W_2$ has a larger inclination than that of the working curve $W_3$ and the measuring accuracy of the spectrum absorbance is better, the sample concentration is obtained based on the working curve $W_2$. For example, when the sample concentration is $C_3$ in the range from $C_2$ to $C_4$ there are three spectrum absorbances $a_4$, $a_5$ and $a_6$ depending on the working curves and the spectrum absorbance $a_5$ is selected. When using the working curve $W_2$ in the range from $C_2$ to $C_4$ the spectrum absorbance is measured with a high accuracy.

In the range of the sample concentration from $C_4$ to $C_n$, as not only the working curve $W_1$ but the working curve $W_2$ is not straight, the sample concentration is obtained from the working curves $W_3$. For example, when the sample concentration is $C_5$ in the range from $C_4$ to $C_n$ there are three spectrum absorbances $a_7$, $a_8$ and $a_9$ depending on the working curves but the spectrum absorbance $a_9$ is selected. When using the working curve $W_3$ in the range from $C_4$ to $C_n$ the spectrum absorbance is measured with a high accuracy the same as the above case and the measuring range of the sample concentration becomes wider.

In the embodiments stated above, the calculation of the combination of the spectrum absorbances $A_1$, $A_2$ and $A_D$ in order to obtain the sample concentrations is executed by the subtraction between $A_1$, $A_2$ and $A_D$. But the calculation of the combination is not limited to the subtraction and all calculations such as the addition, subtraction, multiplication and division which are performed using the spectrum absorbances $A_1$, $A_2$ and $A_D$ may be applied to the present invention.

Figure 1:
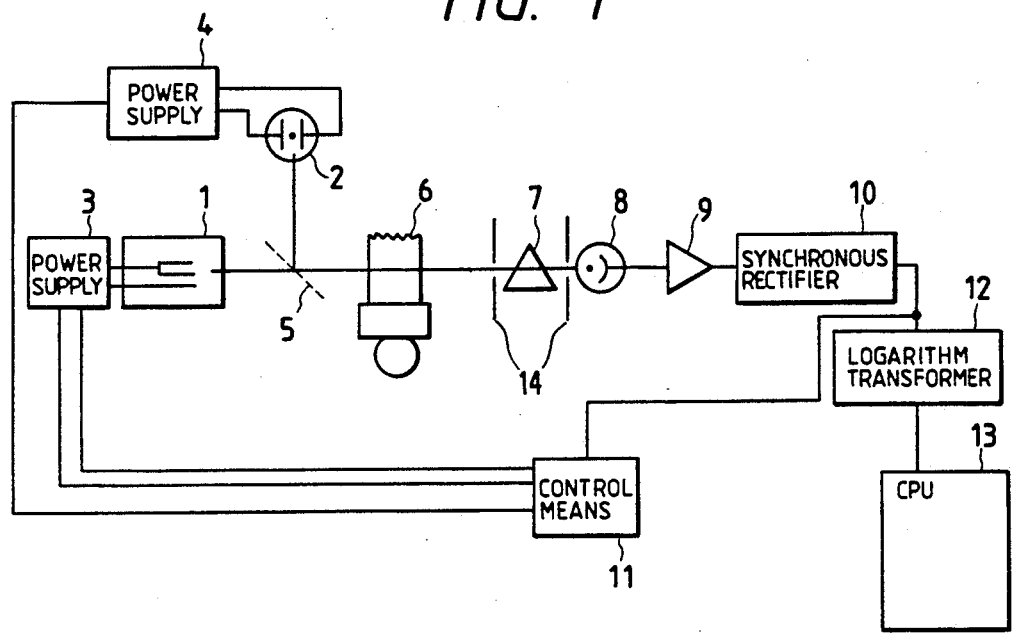
FIG. 1 is a schematic view of an atomic absorption spectrophotometer according to the present invention.

An embodiment of a schematic block diagram of an atomic absorption spectrophotometric apparatus in the present invention will be explained using FIG. 1.

Figure 2:
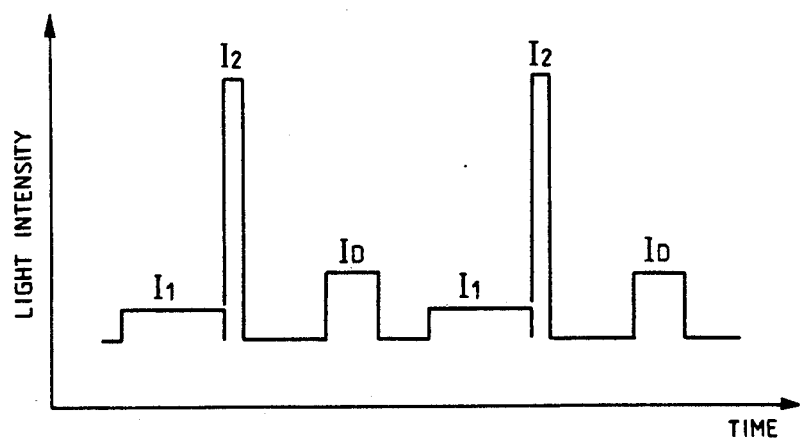
FIG. 2 is a wave form showing light intensity of the specific spectra of the first light source and the continuous spectrum of the second light source in the present invention.

A hollow cathode lamp 1 is supplied with an electric current from an electric power source 3 and emits a specific spectrum corresponding to a specific element and a deuterium lamp 2 is supplied with an electric current from an electric power source 4 and emits a continuous spectrum. The electric currents of the electric power sources 3 and 4 are controlled by a control means 11. That is to say, the control means 11 controls the electric power sources 3 and 4 so as to flow a small current $I_1$ and a large current $I_2$ into the hollow cathode lamp 1 and to flow a current $I_D$ into the deuterium lamp 2 in a constant cycle during respective predetermined periods as shown in FIG. 2. For example, the current of about 10 mA as the small current $I_1$ or the current of 200 to 400 mA as the large current $I_2$ is flown. In this way, the hollow cathode lamp 1 and the deuterium lamp 2 emit three kinds of spectra having respective light intensities at respective times.

These spectra advance on the same light axis through a beam combiner 5 and are absorbed corresponding to the specific elements in a vaporized sample region 6. In this embodiment, the sample is vaporized so as to be atomized by using a burner, but other means such as a graphite furnace may be used instead of the burner. Then, the lights from the light sources 1 and 2 are transmitted to a monochromator having a prism 7 and slits 14 and the light having the specific spectrum having a specific wave length is extracted and input into a detector 8. The detector 8 converts the specific spectrum to an electric signal. The electric signal is amplified by an amplifier 9 and is discriminated by a synchronous rectifier 10. The discriminated signal from the synchronous rectifier 10 is logarithmically transformed based on a logarithmic function by a logarithm transformer 12 and at the same time is fed back to the control means 11.

A computer 13 arbitrarily combines the light absorbances $A_1$, $A_2$ and $A_D$ and performs subtraction between the arbitrarily combined two light absorbances, wherein $A_1$ is the light absorbance when the hollow cathode lamp 1 is supplied with the current $I_1$, $A_2$ is the light absorbance when the hollow cathode lamp 1 is supplied with the current $I_2$ and $A_D$ is the light absorbance when the deuterium lamp 2 is supplied with the current $I_D$. The subtraction is always repeatedly performed using the three combinations of $A_1-A_2$, $A_1-A_D$ and $A_2-A_D$ using the computer 13.

Figure 5:
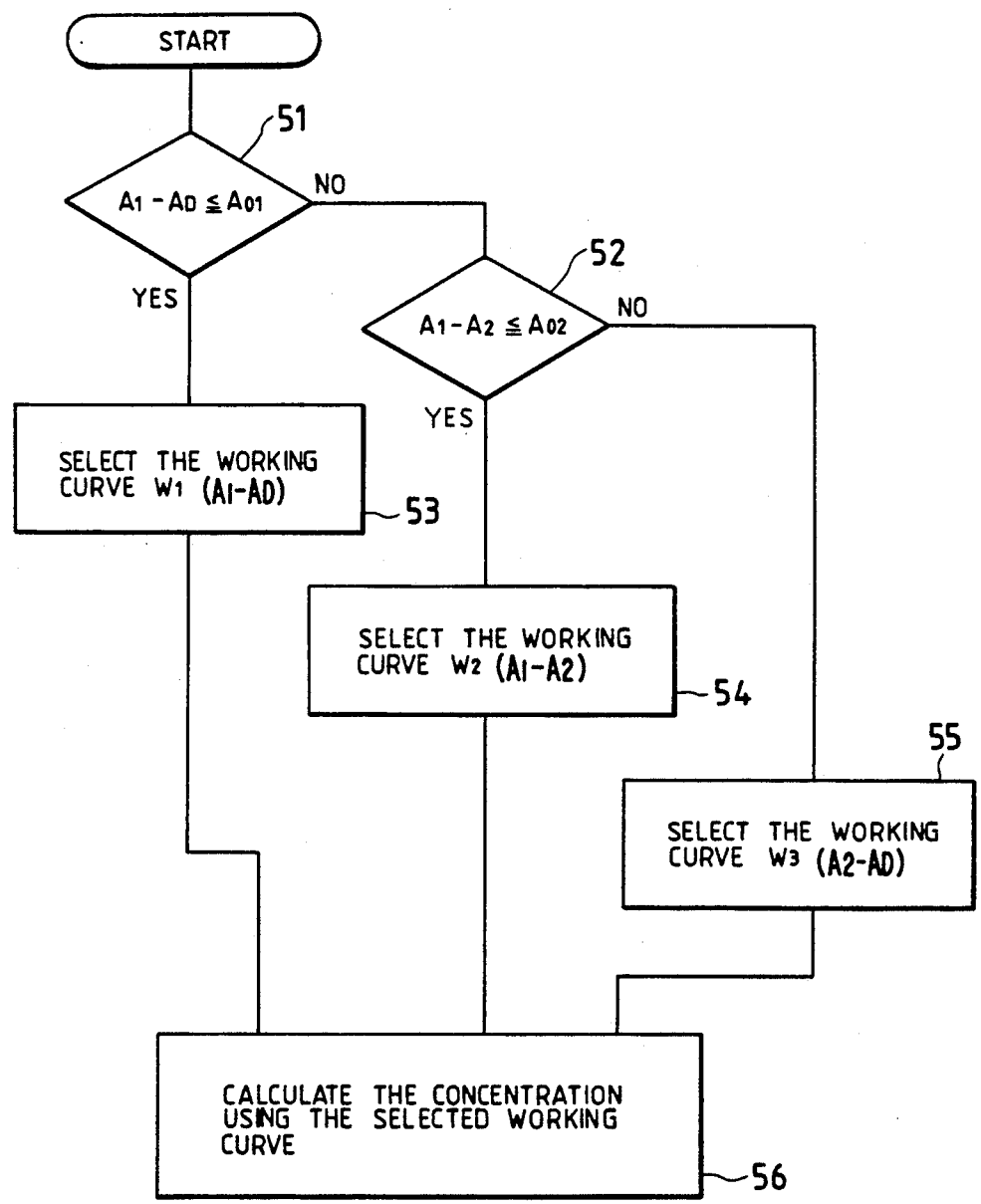
FIG. 5 is a flow chart showing the process by which computer 13 in FIG. 1 calculates the concentration of the sample.

The computer 13 has a function which selects the working curves $W_1$, $W_2$, $W_3$ shown in FIG. 4 and obtains the concentration of the sample by performing the calculation shown in FIG. 5. The working curves $W_1$, $W_2$, $W_3$ are previously memorized in the computer 13, and at first, the subtraction $A_1-A_D$ is performed. When $A_1-A_D$ is not larger than a predetermined value $A_{01}$ (step 51), the working curve $W_1$ is selected (step 53) and the concentration is calculated using the curve $W_1$ (step 56). When $A_1-A_D$ is larger than the predetermined value $A_{01}$ and $A_1-A_2$ is not larger than another predetermined $A_{02}$ (step 52), the working curve $W_2$ is selected (step 54) and the concentration is calculated using the curve $W_2$ (step 56). And when $A_1-A_2$ is larger than the other predetermined value $A_{02}$ (step 52), the working curve $W_3$ is selected (step 55) and the concentration is calculated using the curve $W_3$ (step 56).

In the present invention stated above, as the sample concentration is calculated from at least two spectra emitted from the light source by changing the current thereof and a continuous spectrum, the atomic absorption analysis of the sample can be attained with background correction and over the wide measuring range of the concentration.

I claim:

1. An atomic absorption spectrophotometric apparatus comprising:
    a first light source for emitting a first specific spectrum in response to a first current and for emitting a second specific spectrum in response to a second current, the second current being larger than the first current;
    a second light source for emitting a continuous spectrum;
    an atomizer for atomizing a sample containing a specific element;
    a beam combiner for directing the first specific spectrum and the second specific spectrum emitted from the first light source and the continuous spectrum emitted from the second light source through the atomized sample; p1 a detector for detecting the first specific spectrum, the second specific spectrum, and the continuous spectrum after passage through the atomized sample; and
    computing means for obtaining a first specific spectrum absorbance, a second specific spectrum absorbance, and a continuous spectrum absorbance from outputs of the detector, and for obtaining a concentration of the specific element on the basis of at least one predetermined combination of absorbances selected from the first specific spectrum absorbance, the second specific spectrum absorbance, and the continuous spectrum absorbance.

2. An atomic absorption spectrophotometric apparatus as defined in claim 1, wherein the computing means obtains the concentration of the specific element on the basis of at least one difference between two absorbances selected from the first specific spectrum absorbance, the second specific spectrum absorbance, and the continuous spectrum absorbance.

3. An atomic absorption spectrophotometric apparatus as defined in claim 1, wherein the first light source is a hollow cathode lamp and the second light source is a deuterium lamp.

4. An atomic absorption spectrophotometric apparatus according to claim 3, wherein the first current is about 10 mA and the second current is 200 to 400 mA.

5. An atomic absorption spectrophotometric method comprising the steps of:
    (a) emitting a first specific spectrum from a first light source in response to a first current and emitting a second specific spectrum from the first light source in response to a second current, the second current being larger than the first current;
    (b) emitting a continuous spectrum from a second light source;
    (c) directing the first specific spectrum, the second specific spectrum, and the continuous spectrum through an atomized sample containing a specific element;
    (d) detecting the first specific spectrum, the second specific spectrum, and the continuous spectrum after passage through the atomized sample; and
    (e) obtaining a first specific spectrum absorbance, a second specific spectrum absorbance, and a continuous spectrum absorbance on the basis of the detected first specific spectrum, the detected second specific spectrum, and the detected continuous spectrum, and obtaining a concentration of the specific element on the basis of at least one predetermined combination of absorbances selected from the first specific spectrum absorbance, the second specific spectrum absorbance, and the continuous spectrum absorbance.

6. An atomic absorption spectrophotometric method as defined in claim 5, wherein the concentration of the specific element is obtained on the basis of at least one difference between two absorbances selected from the first specific spectrum absorbance, the second specific spectrum absorbance, and the continuous spectrum absorbance.

7. An atomic absorption spectrophotometric method as defined in claim 5, wherein the first specific spectrum and the second specific spectrum are emitted from a hollow cathode lamp energized by the first current and the second current, respectively, and the continuous spectrum is emitted from a deuterium lamp.

8. An atomic absorption spectrophotometric method according to claim 7, wherein the first current is about 10 mA and the second current is 200 to 400 mA.

9. An atomic absorption spectrophotometric apparatus comprising:
    a first light source for emitting a first specific spectrum in response to a first current and for emitting a second specific spectrum in response to a second current, the second current being larger than the first current;
    a second light source for emitting a continuous spectrum;
    an atomizer for atomizing a sample containing a specific element;
    a beam combiner for directing the first specific spectrum and the second specific spectrum emitted from the first light source and the continuous spectrum emitted from the second light source through the atomized sample;
    a detector for detecting the first specific spectrum, the second specific spectrum, and the continuous spectrum after passage through the atomized sample; and
    computing means for obtaining a first specific spectrum absorbance $A_1$, a second specific spectrum absorbance $A_2$, and a continuous spectrum absorbance $A_D$ from outputs of the detector, and for obtaining a concentration of the specific element on the basis of differences $A_1-A_2$, $A_1-A_D$, and $A_2-A_D$.

10. An atomic absorption spectrophotometric method comprising the steps of:
    (a) emitting a first specific spectrum from a first light source in response to a first current and emitting a second specific spectrum from the first light source in response to a second current, the second current being larger than the first current;
    (b) emitting a continuous spectrum from a second light source;

(c) directing the first specific spectrum, the second specific spectrum, and the continuous spectrum through an atomized sample containing a specific element;
(d) detecting the first specific spectrum, the second specific spectrum, and the continuous spectrum after passage through the atomized sample; and
(e) obtaining a first specific spectrum absorbance, a second specific spectrum absorbance, and a continuous spectrum absorbance on the basis of the detected first specific spectrum, the detected second specific spectrum, and the detected continuous spectrum, and obtaining a concentration of the specific element on the basis of differences $A_1 - A_2$, $A_1 - A_D$, and $A_2 - A_D$.

* * * * *